United States Patent

Robba et al.

[11] 4,005,095
[45] Jan. 25, 1977

[54] SUBSTITUTED THIENYL-ACETIC ACID ESTERS

[75] Inventors: Max Fernand Robba; Michel Emile Marie Aurousseau, both of Paris, France

[73] Assignee: Innothera, Arcueil, France

[22] Filed: May 20, 1975

[21] Appl. No.: 579,069

[30] Foreign Application Priority Data

May 30, 1974 France .............................. 74.18747

[52] U.S. Cl. ...................... 260/293.68; 260/326.35; 260/332.2 A; 424/267; 424/274; 424/275
[51] Int. Cl.[2] .............. C07D 409/12; C07D 333/24
[58] Field of Search ................ 260/293.68, 326.35, 260/332.2 A; 424/267, 274, 275

[56] References Cited

UNITED STATES PATENTS 2,541,634   2/1951   Blicke ........................... 260/326.35

FOREIGN PATENTS OR APPLICATIONS 5,504M   10/1967   France ............................. 260/293.68

OTHER PUBLICATIONS

Lands et al., J. Pharmacol. & Exptl. Thereof. 117 : 334, 339 (1956).

*Primary Examiner*—Natalie Trousoe
*Assistant Examiner*—Robert T. Bond
*Attorney, Agent, or Firm*—Armstrong, Nikaido & Wegner

[57] ABSTRACT

Substituted thienyl-acetic acid esters of the formula:

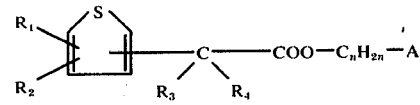

in which $R_1$ and $R_2$ each, independently is H, $CH_3$, $C_2H_5$, $C_3H_7$, $OCH_3$, $SCH_3$, Cl Br or $NO_2$, $R_3$ is phenyl or cyclohexyl and $R_4$ is H, or $R_3$ and $R_4$ together are cyclohexylidene, n is 2 or 3, and A is monoalkylamino or dialkylamino, each alkyl radical having 1 to 4 carbon atoms, or amino derived from a cycloalkylamine of 5 to 7 chain members which may contain an additional hetero-atom, provided that each of $R_1$ and $R_2$ is not H if $R_3$ is phenyl or cyclohexyl and $R_4$ is H, racemates, optical isomers, and their pharmaceutically acceptable acid addition salts and quaternary ammonium salts obtained with alkyl halides, have marked activity as peripheral vasodilators, platelet aggregation inhibitors, spasmolytic agents, coronary and cerebral vasodilators, and papaverine-like activity.

5 Claims, No Drawings

SUBSTITUTED THIENYL-ACETIC ACID ESTERS

The present invention relates to substituted thienyl-acetic acid esters, to processes for their preparation, to compositions containing them, and to their use in therapy.

Special Medicament Pat. Spec. No. 5,504M and French Pat. Spec. No. 1,460,571 describe aminated esters of thienyl-acetic acids. French Pat. Spec. Nos. 2,176,473 and 2,219,776 disclose N-hexamethyleneimino-alkyl derivatives of substituted acetic acids.

New derivatives of thienyl-acetic acids have now been discovered which exhibit valuable therapeutic activity in the field of papaverine-like agents, peripheral vasodilators, platelet aggregation inhibitors, spasmolytic agents and coronary and cerebral vasodilators.

According to the present invention, there are provided compounds corresponding to the formula:

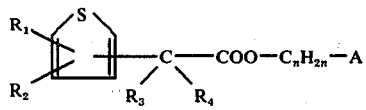  (I)

in which $R_1$ and $R_2$ each independently denotes H, $CH_3$, $C_2H_5$, $C_3H_7$, $OCH_3$, $SCH_3$, Cl, Br or $NO_2$, n is 2 or 3, $R_3$ is phenyl or cyclohexyl and $R_4$ is H, or $R_3$ and $R_4$ together represent cyclohexylidene, and A is monoalkylamino or dialkylamino, the or each alkyl radical having 1 to 4 carbon atoms, or amino derived from a cycloalkylamine of 5 to 7 chain members and may contain an additional hetero-atom, provided that each of $R_1$ and $R_2$ is not H if $R_3$ is phenyl or cyclohexyl and $R_4$ is H.

These compounds can be in the form of racemates or of optically active isomers.

The compounds of the present invention form salts with pharmaceutically acceptable acids and quaternary ammonium salts with alkyl halides.

Preferred compounds of the present invention are those in which $R_1$ and $R_2$ each are H and $R_3$ and $R_4$ together are cyclohexylidene, or $R_1$ is $CH_3$, $R_2$ and $R_4$ each are H and $R_3$ is phenyl or cyclohexyl, and A is diethylamino, pyrrolidino or piperidino.

According to a further aspect of the present invention, the compounds of formula I can be prepared by reacting thienyl-acetic acids of the formula:

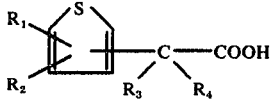  (II)

in which $R_1$, $R_2$, $R_3$ and $R_4$ are as hereinbefore defined, or their alkali metal salts, with an aminoalkyl halide of the formula $X-C_nH_{2n}-A$, in which X is halogen and the other symbols are as hereinbefore defined. When the acid of formula (II) is employed, the compound of formula (I) is obtained directly as its halide addition salt.

According to another aspect of this invention, the compounds of formula (I) can be prepared by reacting a reactive functional derivative of the acid of formula II (for example a halide, anhydride or lower [i.e. of 1 to 6 carbon atoms] alkyl ester) with an amino alcohol of the formula $HO-C_nH_{2n}-A$.

The condensation reactions described above can be carried out by heating in an anhydrous organic diluent of low polarity. Generally, a mixture of equimolecular proportions, of the acid of formula (II), or one of its functional derivatives, and an aminoalkyl chloride is heated under reflux in, for example, anhydrous isopropanol for 15 to 20 hours. The alcohol can then be removed under reduced pressure and the residue recrystallised from a solvent or solvent mixture.

The compounds of the formula (I) can be isolated in the form of racemates or of optically active compounds.

In order to obtain salts other than the hydrochlorides, the hydrochloride salt is treated with an aqueous alkaline solution to displace the hydrochloric acid, the product is extracted with an immiscible organic solvent, and the desired salt obtained with a suitable inorganic or organic acid.

The thienyl-acetic acids of the formula (II) can be synthesised in various ways. For example, the cyclohexylidene-thienyl-acetic acids of the formula (IIA) can be prepared by dehydration of cyclohexyl-thienyl-glycollic acids of the formula (III) by, for example, thionyl chloride, phosphorus trichloride, phosphorus oxychloride or sulphuryl chloride:

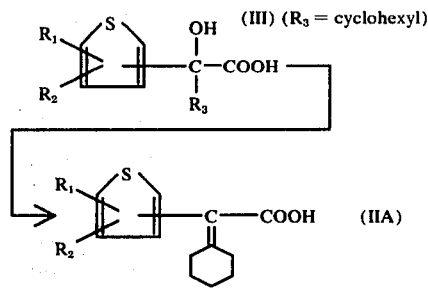

or catalytic

Further the thienyl-acetic acids of the formula (IIB), required for the synthesis of the esters, of formula (I) in which $R_4$ is H, can be prepared by reduction of thienyl glycollic acids of formula (III) using customary chemical or cayalytic reducing agents. The reduction is usually performed by heating the glycollic acid under reflux in a mixture of acetic acid, hydrochloric acid and stannous chloride:

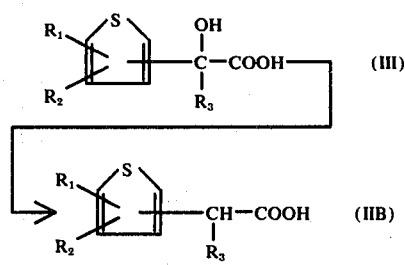

When $R_1$ and/or $R_2$, in the compounds of formula (II), is Cl, Br or $NO_2$, the syntheses can be carried out by electrophilic substitution of the cyclohexyl- and phenyl-thienylacetic acids by the usual halogenation and nitration agents.

The thienylacetic acids of the formula (II) are crystalline solids which are usually soluble in aqueous solutions of alkali metal hydroxides or alkali metal carbonates and in organic solvents such as alcohols, acetone and chloroform.

The acids of formula (III) can be prepared either by reacting organometallic derivatives (such as phenyllithium, cyclohexyl-lithium, phenyl-magnesium bromide and cyclohexyl-magnesium bromide) with the appropriate thienylglyoxylic acids, or by condensing the appropriate thienyllithium or thienyl-magnesium bromide with phenyl-glyoxylic acid or cyclohexyl-glyoxylic acid.

The following Examples 1 to 9 illustrate the preparation of the thienyl-glycollic acids of formula (III), Examples 10 to 19 illustrate the preparation of the thienylacetic acids of formula (II) and Examples 20 to 25 illustrate the preparation of the compounds of the present invention. Temperatures are in ° C and percentages are by weight.

EXAMPLE 1

2,5-Dimethyl-thienyl-3)-phenyl-glycollic acid.

A solution of 29.3 g of (2,5-dimethyl-thienyl-3)-glyoxylic acid and 18 g of phenyl-lithium in 250cm$^3$ of ethyl ether is heated under reflux for 1 hour, with stirring. The mixture is poured onto crushed ice, acidified with hydrochloric acid and extracted repeatedly with ether. The extract is dried over sodium sulphate and evaporated to dryness in vacuo. The residue is recrystallised from ethyl ether.

Yellow crystals, melting point = 114°; weight = 20.8 g; yield 80%.

EXAMPLE 2

(2,5-Dimethyl-thienyl-3)-cyclohexyl-glycollic acid.

A solution of 8.4 g of (2,5-dimethyl-thienyl-3)-glyoxylic acid and 8 g of cyclohexyl-lithium in 200 cm$^3$ of ether is stirred for 1 hour at −30° and then heated under reflux for 1 hour. The mixture is hydrolysed with crushed ice, acidified and extracted with ether.

White crystals, melting point 72°; crystallisable from petroleum ether; weight = 5g; yield 40%.

EXAMPLE 3

(2-Methyl-thienyl-3)-cyclohexyl-glycollic acid.

A solution of n-butyl-lithium in 200 cm$^3$ of ether is prepared at 0° under nitrogen from 33 g of n-butyl bromide and 3.3 g of lithium. It is cooled to −70° and a solution of 16 g of 2-methyl-3-bromo-thiophene in 50 cm$^3$ of ether is added with stirring. The mixture is stirred for 1 hour 30 minutes, and a solution of 9 g of cyclohexyl-glyoxylic acid in 50 cm$^3$ of ether is then added, and the whole is stirred for 1 hour at −70°. It is left for 2 hours at ambient temperature and then hydrolysed by pouring onto crushed ice, and the aqueous phase is decanted and acidified. The product is extracted with ether.

White crystals, melting point = 136°; crystallisable from petroleum ether; weight = 16 g; yield 70%.

EXAMPLE 4

(4-Methylthio-thienyl-3)-cyclohexyl-glycollic acid.

A solution of n-butyl-lithium in 200 cm$^3$ of ether is prepared at 0° under nitrogen from 33 g of n-butyl bromide and 3.3 g of lithium. It is cooled to −70° and a solution of 16 g of 3-bromo-4-methylthio-thiophene in 50 cm$^3$ of ether is added. The mixture is stirred for 1 hour 30 minutes and a solution of 9 g of cyclohexyl-glyoxylic acid in 50 cm$^3$ of ether is then added. The mixture is left for 12 hours at −70° and then for 2 hours at ambient temperature. It is hydrolysed in an acid medium and extracted with ether.

White crystals, melting point 104°; crystallisable from petroleum ether; weight = 15.3 g; yield 70%.

EXAMPLE 5

(5-Methyl-thienyl-2)-cyclohexyl-glycollic acid.

A solution of 24.5 g of 2-methyl-thiophene in 50 cm$^3$ of ether is added at −20° to a solution of 13 g of n-butyl-lithium in 200 cm$^3$ of ether. The mixture is heated under reflux for 15 minutes and then cooled to −10°, and a solution of 15.6 g of cyclohexyl-glyoxylic acid in 50 cm$^3$ of ether is then added. The mixture is stirred for 4 hours at ambient temperature and hydrolysed in an acid medium.

White crystal, melting point 158°; crystallisable from a 1:1 mixture of petroleum ether and diethyl ether; weight = 17.8 g; yield = 70%.

EXAMPLE 6

(5-Methyl-thienyl-2)-phenyl-glycollic acid.

The procedure of Example 5 is followed employing phenyl-glyoxylic acid, to give white crystals; melting point = 124°; crystallisable from a 3:2 mixture of petroleum ether and diethyl ether; yield = 75%.

EXAMPLE 7

(5-Ethyl-thienyl-2)-cyclohexyl-glycollic acid.

The procedure of Example 5 is followed employing 2-ethyl-thiophene and cyclohexyl-glyoxylic acid, to give white crystals; melting point = 156°; crystallisable from ether; yield = 70%.

EXAMPLE 8

(5-n-Propyl-thienyl-2)-cyclohexyl-glycollic acid.

The procedure of Example 5 is followed employing 2-n-propyl-thiophene and cyclohexyl-glyoxylic acid, to give white crystals; melting point = 142°; crystallisable from a 1:2 mixture of diethyl ether and petroleum ether; yield = 70%.

EXAMPLE 9

(5-Methoxy-thienyl-2)-cyclohexyl-glycollic acid.

The procedure of Example 5 is followed employing 2-methoxy-thiophene and cyclohexyl-glyoxylic acid, to give white crystals; melting point = 164°; crystallisable from a 1:3 mixture of diethyl ether and hexane; yield = 70%.

EXAMPLE 10

(2,5-Dimethyl-thienyl-3)-phenylacetic acid.

A solution of 2 g of (2,5-dimethyl-thienyl-3)-phenylglycollic acid and of 7.6 g of stannous chloride in a mixture of 8 cm$^3$ of 10N hydrochloric acid and 4 cm$^3$ of acetic acid is heated under reflux for 30 minutes. It is poured onto iced water and extracted with ether. The ether extract is extracted with a 20% solution of sodium carbonate in water, which is then acidified and extracted with ether.

White crystals; melting point = 89°; recrystallisable from a 1:3 mixture of diethyl ether and hexane; weight = 1.7 g; yield = 90%.

EXAMPLE 11

(2,5-Dimethyl-thienyl-3)-cyclohexyl-acetic acid.

A solution of 2 g of (2,5-dimethyl-thienyl-3)-cyclohexyl-glycollic acid and of 7.6 g of stannous chloride in a mixture of 8 cm³ of 10N hydrochloric acid and of 4 cm³ of acetic acid is heated under reflux for 30 minutes. It is hydrolysed by pouring onto crushed ice and extracted with ether, and the ether is extracted with an aqueous 20% solution of sodium carbonate. This solution is acidified and extracted with ether.

White crystals; melting point = 210°; crystallisable from a 1:3 mixture of diethyl ether and hexane; sublimable at 180° under 1 mm; weight = 1.5 g; yield = 80%.

EXAMPLE 12

(2-Bromo-thienyl-3)-cyclohexyl-acetic acid.

A solution of 11.2 g of (thienyl-3)-cyclohexyl-acetic acid and of 8 g of bromine in 50 cm³ of chloroform is heated under reflux for 1 hour. It is evaporated to dryness in vacuo and petroleum ether is added to crystallise the oily residue.

White crystals; melting point = 132°; crystallisable from petroleum ether; weight = 13.6 g; yield = 90%.

EXAMPLE 13

(5-Nitro-thienyl-3)-cyclohexyl-acetic acid.

A solution of 2 g of (thienyl-3)-cyclohexyl-acetic acid and of 8 cm³ of fuming nitric acid in 50 cm³ of chloroform is stirred for 10 minutes at −5°. It is poured onto ice, the chloroform is decanted and the aqueous phase is extracted with chloroform. The combined organic phases are dried over sodium sulphate and evaporated to dryness.

Yellow crystals; melting point = 148°; crystallisable from acetonitrile; weight = 2.16 g; yield = 90%.

EXAMPLE 14

(2.5-Dinitro-thienyl-3)-cyclohexyl-acetic acid.

A solution of 5 g of (thienyl-3)-cyclohexyl-acetic acid in a mixture of 20 cm³ of fuming nitric acid and of 15 cm³ of sulphuric acid is stirred for 15 minutes at −5°. It is poured onto 100 g of crushed ice and the precipitate is filtered off.

Yellow crystals; melting point = 212°; crystallisable from acetonitrile; weight = 6.6 g; yield 95%.

EXAMPLE 15

(2-Methyl-thienyl-3)-cyclohexyl-acetic acid.

A solution of 5 g of (2methyl-thienyl-3)-cyclohexyl-glycollic acid and of 18 g of stannous chloride in a mixture of 20 cm³ of 10N hydrochloric acid and 10 cm³ of acetic acid is heated under reflux for 30 minutes. It is hydrolysed by pouring onto iced water and the product is filtered off and recrystallised from petroleum ether.

White crystals; melting point = 112°; weight = 3.75 g; yield = 80%.

EXAMPLE 16

(5-Methyl-thienyl-2)-cyclohexyl-acetic acid.

The procedure of Example 15 is followed in which (5-methyl-thienyl-2)-cyclohexyl-glycollic acid is reduced.

White crystals; melting point = 118°; crystallisable from a 1:1 mixture of petroleum ether and diethyl ether yield = 80%.

EXAMPLE 17

(5-Methyl-thienyl-2)-phenylacetic acid.

The procedure of Example 15 is followed in which (5-methyl-thienyl-2)-phenyl-glycollic acid is reduced.

Yellow crystals; melting point = 111°; crystallisable from cyclohexane; yield = 80%.

EXAMPLE 18

(5-n-Propyl-thienyl-2)-cyclohexyl-acetic acid.

The procedure of Example 15 is followed in which (5-n-propyl-thienyl-2)-cyclohexyl-glycollic acid is reduced.

White crystals; melting point = 78°; crystallisable from a 1:2 g of diethyl ether and petroleum ether; yield = 60%.

EXAMPLE 19

Cyclohexylidene-(thienyl-3)-acetic acid.

A solution of 3 g of cyclohexyl-thienyl-glycollic acid and of 2.4 g of phosphorus oxychloride in 100 cm³ of toluene is heated under reflux for 1 hour 30 minutes. It is evaporated to dryness in vacuo, the residue is hydrolysed with ice and the mixture is extracted with diethyl ether.

White crystals; melting point = 146°; crystallisable from a 1:2 mixture of ether and hexane; weight = 2 g; yield = 70%.

EXAMPLE 20

3-Diethylaminopropyl (5-methyl-thienyl-2)-cyclohexyl-acetate (hydrochloride).

A solution of 2 g of (5-methyl-thienyl-2)-cyclohexyl-acetic acid prepared according to Example 16 and of 1.30 g of 3 -diethylamino-1-chloro-propane in 50 cm³ of isopropanol is heated under reflux for 17 hours. It is evaporated to dryness in vacuo and the residue is crystallised from diethyl ether to give the hydrochloride salt.

White crystals; melting point = 136°; crystallisable from a 2:1 mixture of ether and acetonitrile; weight = 2.27 g; yield = 70%.

EXAMPLE 21

3-Pyrrolidino-propyl (5-methyl-thienyl-2)-phenyl-acetate (oxalate).

A solution of 3 g of (5-methyl-thienyl-2)-phenyl-acetic acid prepared according to Example 17 and of 2.2 g of 3-pyrrolidino-1-chloro-propane is heated under reflux for 17 hours. It is evaporated to dryness in vacuo and 50 cm³ of a N aqueous solution of sodium hydroxide is added to the residue. The product is extracted with ether and converted to the oxalate by heating under reflux, in solution in ethanol, with oxalic acid.

Beige crystals; melting point = 162°; crystallisable from acetonitrile; weight = 2.64 g; yield = 60%.

EXAMPLE 22

3-Diethylaminopropyl (2-methyl-thienyl-3)-cyclohexyl-acetate hydrochloride).

A solution of 2.38 g of (2-methyl-thienyl-3)-cyclohexyl-acetic acid prepared according to Example 15 and of 1.50 g of 3-diethylamino-1-chloro-propane in 50 cm³ of isopropanol is heated under reflux for 17 hours. It is evaporated to dryness in vacuo and the residue is recrystallised.

White crystals; melting point = 134°; crystallisable from a 2:1 mixture of ether and acetonitrile; weight = 2.9 g; yield = 75%.

EXAMPLE 23

2-Piperidino-ethyl cyclohexylidene-(thienyl-3)-acetate (hydrochloride).

The procedure of Example 22 is followed using cyclohexylidene-thienylacetic acid prepared according to Example 19, and piperidino-chloroethane.

White crystals; melting point = 210°; crystallisable from a 1:3 mixture of diethyl ether and hexane; yield = 45%.

EXAMPLE 24

3-Piperidino-propyl cyclohexylidene-(thienyl-3)-acetate hydrochloride).

The procedure of Example 22 is followed using cyclohexylidene-thienyl-acetic acid prepared according to Example 19 and 3-piperidino-1-chloro-propane.

White crystls; melting point = 201°; crystallisable from acetonitrile; yield = 40%.

EXAMPLE 25

2-Pyrrolidino-isopropyl cyclohexylidene-(thienyl-3)-acetate (mono-iodomethylate).

The procedure of Example 22 is followed using cyclohexylidene-thienyl-acetic acid and 2-pyrrolidino-1-chloro-isopropane.

White crystals; melting point = 136°; crystallisable from acetone; yield = 40%.

The toxicity and spasmolytic properties of the thienyl-acetic acid esters of the formula (I) have been demonstrated in the following tests.

ACUTE TOXICITY

The acute toxicity was evaluated by intraperitoneal administration to mice. The products were suspended in a dilute pseudo-solution of carboxymethyl-cellulose. The Table which follows shows the 50% lethal dose (LD 50) in milligrams per kilogram of body weight.

The mortality was checked over the course of the 7 days which followed the treatment.

SPASMOLYTIC ACTIVITY

The spasmolytic activity was studied on the rat duodenum (1) or on the guinea pig ileum (2), kept alive in an aerated Tyrode solution heated to 38° C, in accordance with the technique of MAGNUS (Archiv. Ges. Physiol., 1905, 180, 1–71).

(1) The contracting agent used was barium chloride and the reference antagonistic agent was papaverine hydrochloride (R).

The activity of the compounds tested (X) was expressed relative to that of the reference agent chosen (R), by calculating the ratio of their 50% efficient doses (ED 50), which are defined as the concentration which causes a 50% inhibition of the contraction.

The results obtained, which are shown in the Table, shown that the compounds of the invention have a marked spasmolytic activity of the papaverine type, greater than or at least equal to that of the reference agent chosen, because they are effective at lower doses:

$$\frac{ED\ 50\ R}{ED\ 50\ X} \geq 1.$$

(2) The contracting agent used was acetylcholine chloride and the reference antagonistic agent was atropine sulphate (R).

Again, the activity of the compounds tested (X) was compared with that of the reference agent chosen (R), by calculating the ratio of their ED 50 values.

The results obtained (see the Table) show that the majority of the compounds of the present invention have an atropine-like activity which in most cases is less than that of the reference product:

$$\frac{ED\ 50\ of\ R}{ED\ 50\ of\ X} < 1.$$

The compounds according to the present invention can be used as medicaments in human and animal therapy, as papaverine-like agents, peripheral vasodilators, platelet aggregation inhibitors, spasmolytic agents and coronary and cerebral vasodilators.

TABLE

| Example No. | Acute toxicity in mice, intraperitoneal administration, LD 50 (mg/kg) | SPASMOLYTIC ACTIVITY | | | | | |
|---|---|---|---|---|---|---|---|
| | | PAPAVERINE TYPE | | | ATROPINE TYPE | | |
| | | ED 50 (X) g/ml | ED 50 (R) g/ml | $\frac{ED\ 50\ (R)}{ED\ 50\ (X)}$ | ED 50 (X) g/ml | ED 50 (R) g/ml | $\frac{ED\ 50\ (R)}{ED\ 50\ (X)}$ |
| 20 | 80 | $11 \times 10^{-7}$ | $60 \times 10^{-7}$ | 5.45 | $9 \times 10^{-9}$ | $4.5 \times 10^{-9}$ | 0.50 |
| 21 | 100 | $25.5 \times 10^{-7}$ | $55 \times 10^{-7}$ | 2.16 | $100 \times 10^{-9}$ | $4.75 \times 10^{-9}$ | 0.05 |
| 22 | 80 | $3.8 \times 10^{-7}$ | $75 \times 10^{-7}$ | 19.75 | $11.5 \times 10^{-9}$ | $3.5 \times 10^{-9}$ | 0.32 |
| 23 | 80 | $24 \times 10^{-7}$ | $35 \times 10^{-7}$ | 1.46 | $39 \times 10^{-8}$ | $1.1 \times 10^{-8}$ | 0.02 |
| 24 | 150 | $8 \times 10^{-7}$ | $12.5 \times 10^{-7}$ | 1.56 | $80 \times 10^{-8}$ | $0.45 \times 10^{-8}$ | 0.005 |
| 25 | 80 | $29.5 \times 10^{-7}$ | $30 \times 10^{-7}$ | 1 | $1.2 \times 10^{-10}$ | $3 \times 10^{-10}$ | 2.5 |

The invention also includes within its scope pharmaceutical compositions comprising a compound of the invention in association with a pharmaceutically acceptable carrier.

The compounds of the present invention can be made up in a form suitable for oral, rectal or parenteral administration to man or animals, usually in association with excipients suited to the method of administration

We claim:
1. A compound of the formula:

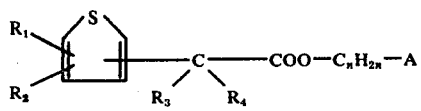

in which $R_1$ and $R_2$ are independently H, $CH_3$, $C_2H_5$, $C_3H_7$, $OCH_3$, $SCH_3$, Cl, Br or $NO_2$, $R_3$ and $R_4$ together are cyclohexylidene, n is 2 or 3, and A is monoalkylamino or dialkylamino, each alkyl radical having 1 to 4 carbon atoms, pyrrolidino or piperidino, racemates, optical isomers, and their pharmaceutically acceptable acid addition salts and quaternary ammonium salts obtained with alkyl halides.

2. A compound according to claim 1, in which $R_1$ and $R_2$ each are H, and A is diethylamino, pyrrolidino or piperidino.

3. A compound according to claim 1 which is 2-piperidino-ethyl cyclohexylidene-(thienyl-3)-acetate and its pharmaceutically acceptable acid addition salts.

4. A compound according to claim 1 which is 3-piperidino-propyl cyclohexylidene-(thienyl-3)-acetate and its pharmaceutically acceptable acid addition salts.

5. A compound according to claim 1 which is 2-pyrrolidino-isopropyl cyclohexylidene-(thienyl-3)-acetate and its pharmaceutically acceptable acid addition salts.

* * * * *